(12) United States Patent
Archat et al.

(10) Patent No.: US 12,303,665 B2
(45) Date of Patent: May 20, 2025

(54) INFUSION DEVICE FOR ADMINISTERING A MEDICAL FLUID TO A PATIENT

(71) Applicant: Fresenius Vial SAS, Brézins (FR)

(72) Inventors: Damien Archat, Grénoble (FR); Mathieu Paoli, La Murette (FR); Philippe Traversaz, Voiron (FR)

(73) Assignee: Fresenius Vial SAS, Brézins (FR)

( * ) Notice: Subject to any disclaimer, the term of this patent is extended or adjusted under 35 U.S.C. 154(b) by 974 days.

(21) Appl. No.: 17/424,466

(22) PCT Filed: Dec. 13, 2019

(86) PCT No.: PCT/EP2019/085157
§ 371 (c)(1),
(2) Date: Jul. 20, 2021

(87) PCT Pub. No.: WO2021/160821
PCT Pub. Date: Aug. 13, 2021

(65) Prior Publication Data
US 2022/0088294 A1 Mar. 24, 2022

(30) Foreign Application Priority Data
Feb. 4, 2019 (EP) ..................................... 19305129

(51) Int. Cl.
*A61M 5/145* (2006.01)
(52) U.S. Cl.
CPC ..... *A61M 5/1456* (2013.01); *A61M 2205/332* (2013.01)
(58) Field of Classification Search
CPC .............. A61M 5/1456; A61M 5/1458; A61M 5/1452; A61M 2205/332; A61M 2205/3317
See application file for complete search history.

(56) References Cited

U.S. PATENT DOCUMENTS

| 6,575,936 B1 * | 6/2003 | Kojima | A61M 5/14526 604/131 |
| 2012/0215170 A1 | 8/2012 | Traversaz et al. | |

(Continued)

FOREIGN PATENT DOCUMENTS

| CN | 201054895 Y | 5/2008 |
| CN | 105664289 A | 6/2016 |
| EP | 3222307 | 9/2017 |

OTHER PUBLICATIONS

International Search Report and Written Opinion, counterpart International Appl. No. PCT/EP2019/085157 (Jan. 28, 2020) (9 pages).

(Continued)

*Primary Examiner* — Tasnim Mehjabin Ahmed
(74) *Attorney, Agent, or Firm* — Cook Alex Ltd.

(57) ABSTRACT

An infusion device (1) for administering a medical fluid to a patient comprises a housing (10), a receptacle (11) arranged on the housing (10) for receiving a syringe (2), a syringe driver (12) movable in a driving direction (P) for acting onto a piston (21) of a syringe (2) received on the receptacle (11), and a drive mechanism (13) for electromotively driving the syringe driver (12) along the driving direction (P), the drive mechanism (13) comprising an electric drive motor (14) and a rotatable drive element (18) operatively coupled to the syringe driver (12) for moving the syringe driver (12) along the driving direction (P). Herein, the drive mechanism (13) comprises a clutch device (16) configured, in a coupled state, to couple the drive device (14) to the drive element (18) such that the drive device (14) is operative to drive the drive element (18) and, in an uncoupled state, to uncouple the drive device (14) from the drive element (18).

12 Claims, 3 Drawing Sheets

(56) References Cited

U.S. PATENT DOCUMENTS

2017/0326293 A1* 11/2017 Sims .................. A61M 5/1458
2018/0326145 A1* 11/2018 Jiang .................. A61M 5/1452

OTHER PUBLICATIONS

Office Action and Search Report (with English-language translation), counterpart Chinese App. No. 201980091250.1 (Feb. 13, 2023) (15 pages).

* cited by examiner

INFUSION DEVICE FOR ADMINISTERING A MEDICAL FLUID TO A PATIENT

The present application is a U.S. National Stage of PCT International Patent Application No. PCT/EP2019/085157, filed Dec. 13, 2019, which claims priority to EP Application Serial No. 19305129.9, filed Feb. 4, 2019, both of which are hereby incorporated herein by reference.

The invention relates to an infusion device for administering a medical fluid to a patient according to the preamble of claim 1 and to a method for operating an infusion device.

An infusion device of this kind comprises a housing, a receptacle arranged on the housing for receiving a syringe, a syringe driver movable in a driving direction for acting onto a piston of a syringe received on the receptacle, and a drive mechanism for electromotively driving the pusher device along the driving direction, the drive mechanism comprising an electric drive motor and a rotatable drive element operatively coupled to the syringe driver to move the syringe driver along the driving direction.

US 2012/0215170 A1 discloses an infusion device in the shape of a syringe pump which, for acting onto a piston of a syringe, comprises a syringe driver driven by a drive mechanism comprising a rotatable spindle. The rotatable spindle is coupled to an electric drive motor such that, by means of the electric drive motor, the spindle can be rotated in order to cause the syringe driver to be longitudinally moved along a driving direction to deliver a medical fluid from a syringe towards a patient. To establish a coupling in between the spindle and the syringe driver, herein, a clutch mechanism is provided which, in a clutched state, engages with the spindle such that in the clutched state the clutch device as a whole is longitudinally moved with respect to the spindle when the spindle rotates. The clutch device can be unclutched from the spindle such that a movement of the syringe driver is possible with respect to and independent of the spindle, for example during installation of a syringe on the infusion device or to exert a manual bolus.

There is a general desire to provide an infusion device implementing an alternative solution for a drive mechanism, in particular offering a simplification in construction and a possible reduction in costs.

It is an object of the instant invention to provide an infusion device having a drive mechanism which can be of simplified construction, yet providing a reliable and exact infusion operation for administering a medical fluid to a patient.

This object is achieved by means of an infusion device comprising the features of claim 1.

Accordingly, the drive mechanism comprises a clutch device configured, in a coupled state, to couple the drive device to the drive element such that the drive device is operative to drive the drive element and, in an uncoupled state, to uncouple the drive device from the drive element.

The infusion device hence uses a drive mechanism comprising an electric drive motor and a rotatable drive element. The electric drive motor is coupled to the rotatable drive element by means of a clutch device, which may assume a coupled state in which an operative connection in between the electric drive motor and the rotatable drive element is established and an uncoupled state in which the operative connection in between the electric drive motor and the rotatable drive element is released. A force transfer in between the electric drive motor and the rotatable drive element hence takes place via the clutch device, wherein a force transfer in between the electric drive motor and the rotatable drive element may be interrupted by transferring the clutching device into its uncoupled state such that the drive element may be rotated freely and independently of the electric drive motor.

The clutch device for example may comprise a first clutch element and a second clutch element, wherein the first clutch element is operatively connected to the electric drive motor and the second clutch element is operatively connected to the drive element. In the coupled state of the clutch device the first clutch element and the second clutch element are in clutching connection with each other such that forces may be transferred in between the first clutch element and the second clutch element and the first clutch element and the second clutch element may be rotated together. In the uncoupled state, in contrast, a free movement of one clutch element with respect to the other clutch element is possible such that the rotatable drive element may be freely rotated with respect to the electric drive motor.

In the coupled state the clutch elements may for example be in frictional contact with each other such that the clutch elements are coupled to each other in a rotationally fixed manner. The clutch device herein may be electromagnetically driven such that the clutch elements may be brought into abutment with each other to transfer the clutch device to the coupled state or may be released from one another in order to transfer the clutch device into its uncoupled state.

In another embodiment the clutch elements are in positive-locking engagement in the coupled state, for example by means of a suitable toothing provided on the first clutch element and the second clutch element, and are released from one another in the unclutched state.

The clutch device may, alternatively, be implemented by a magnetic clutch device in which the clutch elements are operatively connected to each other by magnetic means, that is without frictionally contacting each other, in the coupled state.

In one embodiment, the electric drive motor comprises a drive shaft and a worm screw arranged on the drive shaft. During operation the electric drive motor drives the drive shaft to rotate, the worm screw herein for example engaging with a worm wheel such that by means of the worm screw the worm wheel is rotated. The worm wheel herein may be connected, by means of a shaft, to the first clutch element of the clutch device, such that the electric drive motor by means of the worm wheel acts onto the first clutch element of the clutch device.

The worm wheel together with the worm screw forms a gearing to connect the electric drive motor to the clutch device. In one embodiment, such gearing may be self-locking such that, in the coupled state of the clutch device, the drive mechanism is locked with respect to a movement of the syringe driver in case an external force is applied to the syringe driver. If external forces act onto the syringe driver when the clutch device is in its coupled state, hence, a movement of the syringe driver is prevented in that, due to the self-locking, the drive element cannot be rotated and hence the syringe driver is held in position by means of the drive element. An unintentional movement of the syringe driver due to external forces acting onto the syringe driver hence is effectively prevented. A driving of the drive element is possible, in the clutched state, only by means of the electric drive motor.

In one embodiment, the drive element is formed by a spindle having a screw thread. The drive element is rotatable about a longitudinal axis and, by means of the screw thread formed on the circumferential outside of the spindle, engages for example with a coupling element in the shape of a spindle nut connected to the syringe driver. The engagement of the spindle with the coupling element causes the coupling element to move longitudinally along the drive element when the drive element rotates about its longitudinal axis, a rotational movement of the spindle hence being translated into a longitudinal movement of the coupling element. By means of the longitudinal movement of the coupling element the syringe driver connected to the coupling element is moved, in particular for driving the piston of a syringe received on the receptacle of the infusion device such that a medical fluid is delivered from the syringe through an infusion line connected to the syringe.

The coupling of the syringe driver to the drive element in the shape of the spindle is, in one embodiment, non-releasable. In particular, the clutch device is functionally arranged prior to the spindle (when viewed from the electric drive motor), the clutch device hence serving to couple or uncouple the electric drive motor from the drive element in the shape of the spindle. Hence, when the clutch device is in the uncoupled state and the syringe driver is manually moved for example for installing a syringe on the infusion device, the longitudinal movement of the syringe driver is transferred to the drive element in the shape of the spindle, which correspondingly is rotated when moving the syringe driver.

In one embodiment, the infusion device comprises a control device for controlling the clutch device. The control device in particular may issue control commands to transfer the clutch device from its coupled to its uncoupled state and vice versa. In addition, the control device may be configured to control the electric drive motor and may be configured to evaluate sensing signals of sensor devices for controlling operation.

In one embodiment, the infusion device comprises an actuation device which is user actuatable for transferring the clutch device from one of the coupled state and the uncoupled state to the other of the coupled state and the uncoupled state. The actuation device may for example have the shape of a pushbutton (e.g. comprising a micro-switch), the actuation of the actuation device causing an electrical signal according to which the control device may control the clutch device to be transferred from one state to the other. Alternatively, the actuation device may have the shape of a mechanical device serving to mechanically transfer the clutch device from one state to the other.

In one embodiment, the actuation device, for example in the shape of a pushbutton, is arranged on the syringe driver such that a user may intuitively act onto the actuation device when manually acting onto the syringe driver. A user—who wishes to, for example in the course of installing a syringe on the infusion device, manually move the syringe driver towards the syringe such that the syringe driver is brought into abutment with the piston head of a piston of the syringe—may place one hand on the syringe driver and may actuate the actuation device such that the clutch device is transferred from the coupled state to the uncoupled state, hence allowing for a free manual movement of the syringe driver.

The clutch device, herein, in a rest state may assume the coupled state such that, when the actuation device is not actuated, the syringe driver is held in position, for example due to a self-locking of the drive mechanism or by an additional braking action of a brake device acting onto the drive element or onto another gear element of the drive mechanism. By actuating the actuation device the clutch device may be transferred from the coupled state to the uncoupled state such that the syringe driver is uncoupled from the electric drive motor and the drive chain of the drive mechanism hence is released, allowing for a free manual movement of the syringe driver independent of the electric drive motor.

In particular if the actuation device is implemented by means of a pushbutton, the actuation device may be configured, in case of an actuation, to produce an actuation signal in the shape of an electrical control signal, which may be provided to the control device and may be processed by the control device, causing the clutch device to be transferred from the coupled state to the uncoupled state. A user herein may have to keep actuating the actuation device, for example by pushing a corresponding pushbutton, in order for the clutch device to be maintained in the uncoupled state. Alternatively, a user may have to press the actuation device only once, upon which the clutch device is transferred from the coupled state to the uncoupled state and is maintained in the uncoupled state for a predetermined amount of time or until a particular event occurs. For example, the clutch device may be transferred back to the coupled state in case it is detected, by means of a sensor device, that a contact between the syringe driver and a piston head of a piston of a syringe is established, indicating that during installation a desired operative connection between the syringe driver and the syringe is established.

A sensor device for detecting a contact between the syringe driver and the piston of a syringe may be arranged for example on the syringe driver and may have the shape of a touch sensor, for example comprising a micro-switch or the like. A sensor device of this kind however may also be configured as a force sensor for measuring a force in between the syringe driver and the piston of a syringe, such sensor during operation of the infusion device providing force readings from which a pressure value in the syringe and in an infusion line connected to the syringe may be derived.

During installation, if by means of the sensor device it is detected that the syringe driver has been brought into contact with the piston of the syringe received on the receptacle of the infusion device, a sensor signal may be transmitted to the control device and may be processed by the control device to transfer the clutch device from its uncoupled state to the coupled state such that the drive mechanism is brought into an operative state for starting an infusion operation and, in particular, for effectively preventing an uncontrolled movement of the syringe driver and the piston of the syringe. In case a user wishes to provide a manual bolus, the user may (again) actuate the actuation device, causing the clutch device to be transferred from the coupled state to the uncoupled state such that a user may act onto the syringe driver for moving the piston of the syringe received on the receptacle of the infusion device, wherein after the manual bolus the clutch device is transferred back to its coupled state, for example after a predetermined time or after it is detected that a manual movement of the syringe driver has been terminated or after a calculated volume of infusion has been reached.

The idea underlying the invention shall subsequently be described in more detail with respect to the embodiments shown in the figures. Herein:

Figure 1:
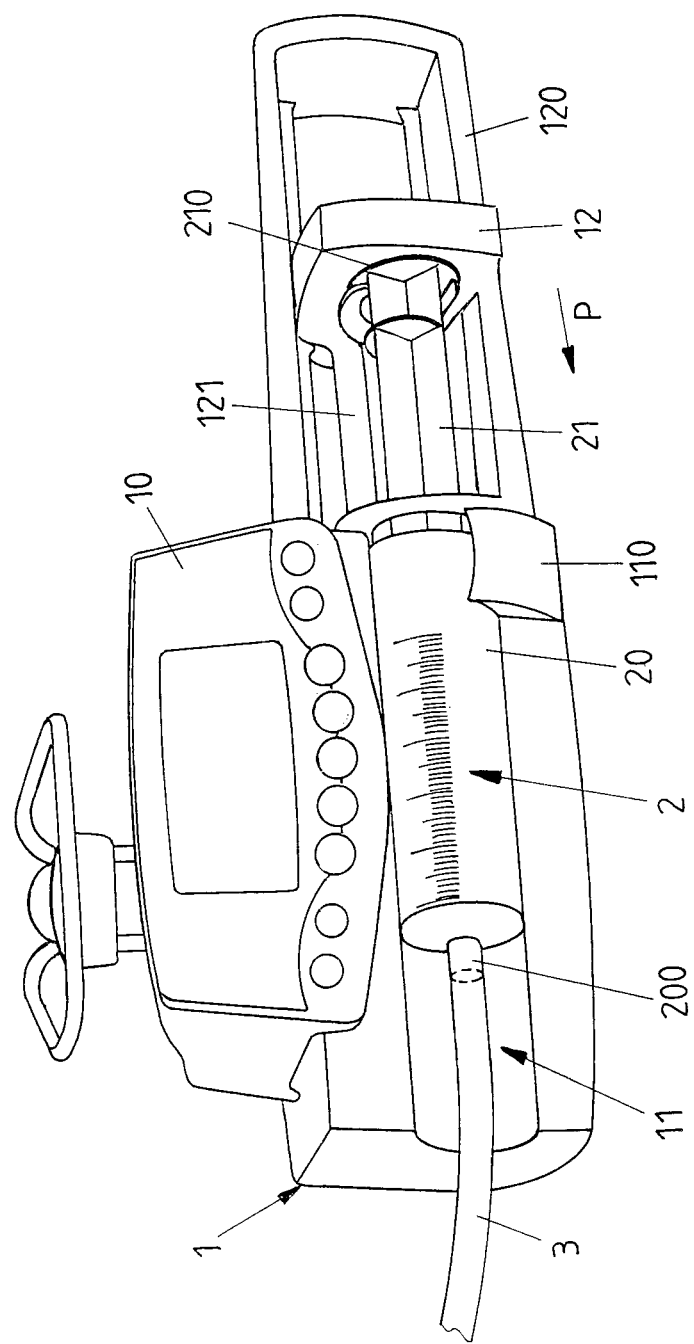
FIG. 1 shows a view of an embodiment of an infusion device in the shape of a syringe pump.

FIG. 1 shows an infusion device 1 in the shape of a syringe pump having a housing 10 and a receptacle 11 arranged on the housing 10 to receive a syringe 2 therein.

The syringe 2 comprises a cylindrical tube 20 which, when installing the syringe 2 on the infusion device 1, contains a medical liquid, for example a medication or a solution for the parenteral feeding, to be infused to a patient. The cylindrical tube 20 is connected, via a connector 200, to an infusion line 3 which may extend from the syringe 2 towards a patient for infusing the medical liquid to the patient.

For installing the syringe 2 on the receptacle 11 of the infusion device 1, the cylindrical tube 20 of the syringe 2 is placed in the receptacle 11 and is mechanically connected to the housing 10 by means of a fixation device 110. By means of the fixation device 110, for example constituted by a releasable clamp element, the cylindrical tube 20 is secured within the receptacle 11 such that the cylindrical tube 20 is held in position on the receptacle 11.

The syringe 2 comprises a piston 21 which, for delivering medical fluid contained in the cylindrical tube 20, can be pushed into the cylindrical tube 20 in a driving direction P. For this, the infusion device 1 comprises a syringe driver 12 movably arranged within a guide device 120 and connected to a drive mechanism (which subsequently shall be described with relation to FIGS. 2 and 3) via a connecting rod 121.

For operating the infusion device 1, the syringe 2 is installed on the infusion device 1 and the syringe driver 12 is (e.g., manually) moved towards a piston head 210 of the piston 21 until the syringe driver 12 comes into abutment with the piston head 210. For performing an infusion process the syringe driver 12 is then electrically moved in the driving direction P to move the piston 21 into the cylindrical tube 20 for delivering the medical fluid contained in the cylindrical tube 20 via the infusion line 3 towards the patient.

Figure 2:
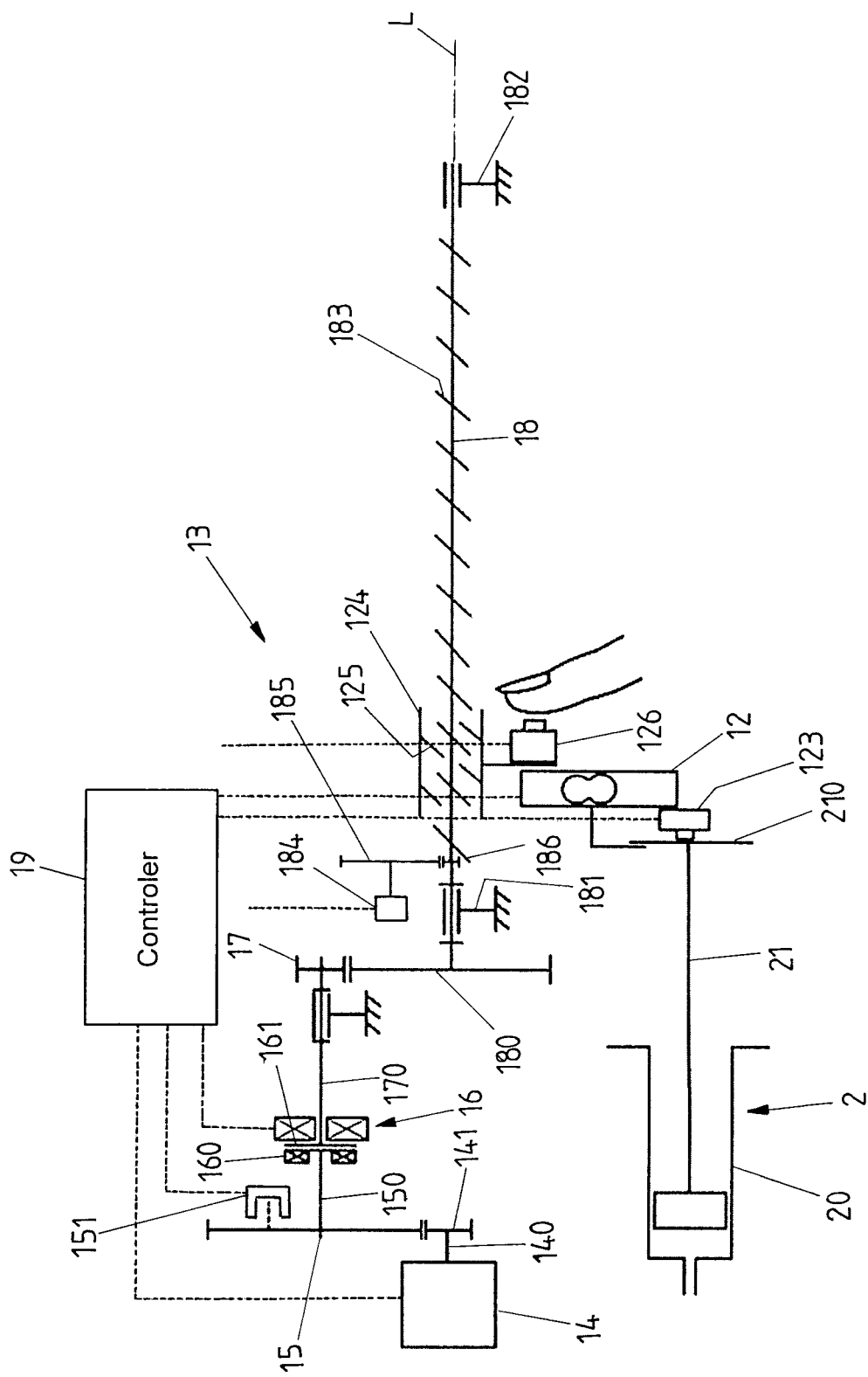
FIG. 2 shows a schematic drawing of a drive mechanism for driving a syringe driver of the infusion device.

The syringe driver 12 is driven by a drive mechanism 13, which, according to one embodiment, is schematically illustrated in FIG. 2.

The drive mechanism 13 comprises a rotatable drive element 18 in the shape of a spindle, which is connected to the syringe driver 12 via a coupling element 124. The drive element 18 in the shape of the spindle is rotatably mounted, about a longitudinal axis L, with respect to the housing 10 by means of bearings 181, 182 and comprises an outer screw thread 183 by means of which the drive element 18 is in engagement with an internal screw thread 125 formed on the coupling element 124, the coupling element 124 having the shape of a spindle nut being held rotationally fixed with respect to the housing 10, but being longitudinally movable along the longitudinal axis L on the drive element 18.

Figure 3:
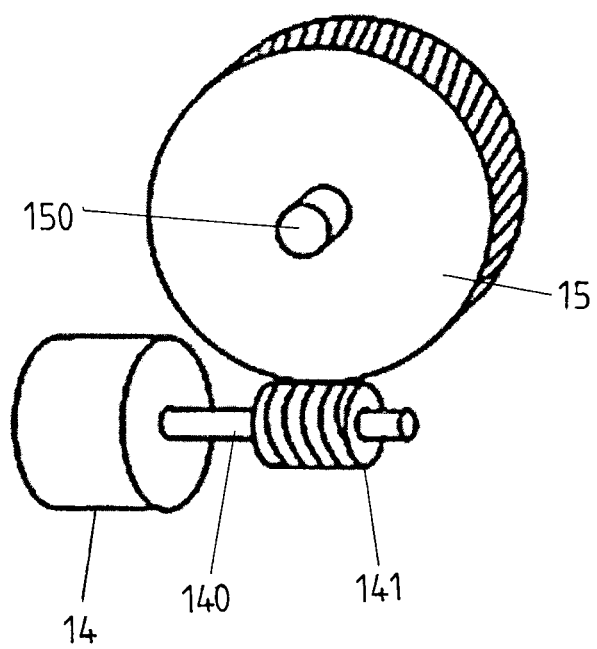
FIG. 3 shows a schematic view of an embodiment of the electric drive motor in operative connection with a gear element for driving the drive mechanism.

The drive mechanism 13 further comprises an electric drive motor 14 having a drive shaft 140 and a gear element 141 for example in the shape of a worm screw, as indicated in FIG. 3, arranged thereon. By means of the gear element 141 the electric drive motor 14 is in operative connection with a gear element 15 in the shape of a worm wheel, as shown in FIG. 3, the gear element 15 being, by means of a shaft 150, connected to a clutch element 160 of a clutch device 16.

The clutch device 16 comprises clutch elements 160, 161, which in a coupled state of the clutch device 16 are in a rotationally fixed connection with each other, for example by frictionally abutting each other. The clutch device 16 may be electromagnetically driven such that the clutch elements 160, 161 are axially movable with respect to each other in order to transfer the clutch device 16 between its coupled state and the uncoupled state.

Whereas the clutch element 160 is associated with the gear element 15 on the side of the electric drive motor 14, the clutch element 161, by means of a shaft 170, is connected to a gear element 17 in the shape of a tooth wheel, which acts onto a gear wheel 180 in the shape of a tooth wheel fixedly connected to the drive element 18.

For operating the infusion device 1, the clutch device 16 is in the coupled state. By operating the electric drive motor 14, hence, a rotational movement of the drive shaft 140 may be transferred to the gear element 15 and the gear wheel 17, by means of which the drive element 18 in the shape of the spindle is driven to rotate about its longitudinal axis L. Such rotation causes, due to the engagement of the coupling element 124 in the shape of the spindle nut with the outer screw thread 183 of the drive element 18, the coupling element 124 to be longitudinally moved along the longitudinal axis L with respect to the drive element 18, such that the syringe driver 12 fixedly connected to the coupling element 124 is moved along the guide 120 formed on the housing 10 of the infusion device 1, as indicated in FIG. 1.

The syringe driver 12 may be connected to the coupling element 124 by means of the connecting rod 121, as shown in FIG. 1.

During regular operation, hence, an electric drive motion of the electric drive motor 14 is transferred to the drive element 18 in the shape of the spindle and via the drive element 18 to the coupling element 124 and the syringe driver 12, causing the syringe driver 12 to be longitudinally moved on the housing 10 for acting onto the piston 21 of a syringe 2 received on the receptacle 11 of the infusion device 1.

The infusion device 1 comprises a control device 19, as schematically indicated in FIG. 2, serving to control the operation of the electric drive motor 14. The control device 19 may in particular be configured to process signals of a sensor device 184 connected to the drive element 18 by means of a gear wheel 185, such sensor device 184 being configured to detect a rotational position of the drive element 18, such that by means of the signals of the sensor device 184 the actual position of the syringe driver 12 may be computed.

In addition, the control device 19 may be configured to control the clutch device 16 for transferring the clutch device 16 between its coupled state and the uncoupled state.

The drive mechanism 13 may have a self-locking configuration. Hence, if the clutch device 16 is in its coupled state the syringe driver 12 is held in position by means of the drive mechanism 13, such that in particular external forces acting onto the syringe driver 12 may not cause an uncontrolled, lateral movement of the syringe driver 12 with respect to the housing 10.

In addition, a detection device 151 in the shape of for example an optocoupler may be provided, the detection device 151 being configured to detect a position/movement of the gear element 15 in order to control the pumping flow rate.

For example for installing a syringe 2 on the receptacle 11 of the infusion device 1 it is desirable to allow a manual, free movement of the syringe driver 12. For example for installation of a syringe 2, thus, the clutch device 16 may be transferred to its uncoupled state, such that the drive chain in between the electric drive motor 14 and the drive element 18 is interrupted. In the uncoupled state of the clutch device 16 the syringe driver 12 may be freely moved independent of the electric drive motor 14 such that, for installing a syringe 2 on the receptacle 11 of the infusion device 1, the syringe driver 12 may manually be approached towards the piston head 210 of the piston 21 of the syringe 2 until the syringe driver 12 is brought into abutment with the piston head 210 of the piston 21.

If the clutch device 16 is in the uncoupled state, hence, a free manual movement of the syringe driver 12 is possible, independent of the electric drive motor 14. The drive element 18 in the shape of the spindle herein is driven to rotate by means of the engagement with the coupling element 124, the screw thread 183 of the drive element 18 and the screw thread 125 of the coupling element 124 having a (relatively large) thread pitch such that a longitudinal movement of the coupling element 124 causes a rotation of the drive element 18.

As schematically indicated in FIG. 2, an actuation device 126 for example in the shape of a pushbutton (e.g. having a micro-switch) may be arranged on the syringe driver 12. A user may act onto the actuation device 126 in order to produce an electrical signal, which is transmitted to the control device 19 and is processed by means of the control device 19 in order to transfer the clutch device 16 from its coupled state to the uncoupled state. Hence, to allow a free manual movement of the syringe driver 12, a user may act onto the actuation device 126, upon which the control device 19 causes the clutch device 16 to be switched from the coupled state (which the clutch device 16 regularly assumes during rest) to the uncoupled state.

During installation, hence, a user may move the syringe driver 12 towards the piston head 210 of the piston 21 if the clutch device 16 is in the uncoupled state. In order to prevent an undesired bolus due to a force applied to the piston 21 during installation, once it is detected that the syringe driver 12 has been brought into abutment with the piston 21 the control device 19 causes the clutch device 16 to be automatically transferred back to the coupled state. For this, a sensor device 123 is arranged on the syringe driver 12, the sensor device 123 being configured to detect a contact in between the syringe driver 12 and piston head 210 of the piston 21. The sensor device 123 may for example have the shape of a touch sensor, for example having a micro-switch or the like. Alternatively, the sensor device 123 may be a force sensor configured to measure a force in between the syringe driver 12 and the piston head 210.

Hence, once the syringe driver 12 has been approached towards the piston 21, the clutch device 16 is transferred to the coupled state, hence locking the syringe driver 12 in its currently assumed position. Now, a fixation device 122 of the syringe driver 12 may be actuated for establishing a fixed connection in between the syringe driver 12 and the piston 21 of the syringe 2, upon which regular infusion operation of the infusion device 1 may start.

If a user wishes to cause a manual bolus during an infusion operation, the user may again press on the actuation device 126, causing the clutch device 16 to be transferred to the uncoupled state, upon which the user may move the syringe driver 12 and hence the piston 21 to apply the bolus. Once the bolus has been finished, the clutch device 16 is transferred back to its coupled state, for example after a predetermined time or after it is detected that the syringe driver 12 is no longer moved or after a calculated volume of infusion has been reached.

During rest, the clutch device 16 is in its coupled state. This ensures that, even in case of power failure, the syringe driver 12 is held in position, hence preventing an undesired free flow due to an uncontrolled movement of the syringe driver 12.

For installing a syringe 2 on the receptacle 11 of the infusion device 1, a user may have to manually move the syringe driver 12, while the clutch device 16 is in the uncoupled state, for moving the syringe driver 12 opposite to the driving direction P for allowing placement of the syringe 2 on the receptacle 11 and for then moving the syringe driver 12 in the driving direction P towards the piston 21 to bring the syringe driver 12 into operative connection with the piston 21.

Installation of a syringe 2 may alternatively take place in an automatic or at least semi-automatic mode.

In an automatic mode, the syringe driver 12 may electromotively be moved first opposite to the driving direction P for allowing placement of the syringe 2 on the receptacle 11 in order to then electromotively move the syringe driver 12 in the driving direction P to establish connection in between the syringe driver 12 and the piston 21. In this case the clutch device 16 is in the coupled state, hence allowing an electromotive movement of the syringe driver 12 driven by the electric drive motor 14.

In a semi-automatic mode a user may have to manually move the syringe driver 12 opposite the driving direction P, while the clutch device 16 is in the uncoupled state, to allow placement of the syringe 2 on the receptacle 11. The approach of the syringe driver 12 towards the piston 21 of the syringe 2 then takes place by electromotively driving the syringe driver 12, such that the operative connection in between the syringe driver 12 and the piston 21 is automatically established. In particular, motion of the syringe driver 12 towards the piston 21 may automatically stop once contact between the syringe driver 12 and the piston 21 has been established, upon which the syringe driver 12 is operatively fixed to the piston 21 by means of the fixation device 122.

The fixation device 122 may be controlled by means of the control device 19, the syringe driver 12 having for example an electromotive mechanism for moving the fixation device 122. Fixation of the syringe driver 12 with respect to the piston 21 hence may take place automatically.

The invention is not limited to the embodiments described above, but may be implemented in an entirely different fashion.

Infusion devices of the kind described herein may serve different purposes and may be constituted to receive syringes of different shape and different size. An infusion device of this kind may in particular not be limited to a particular type of syringe as it may be described herein.

A clutch device as described herein may be driven electromagnetically by moving clutch elements with respect to each other by means of electromagnetic forces. The clutch elements herein may for example frictionally abut in the coupled state, or may be locked with respect to each other in a positive locking manner.

The clutch device, alternatively, may be implemented by a magnetic clutch in which a magnetic coupling of clutch elements is established.

LIST OF REFERENCE NUMERALS

1 Infusion device
10 Housing
11 Receptacle
110 Fixation device
12 Syringe driver
120 Guide device
121 Connecting rod
122 Fixation device 123 Sensor device
124 Coupling element
125 Screw thread
126 Actuation device
13 Drive mechanism
14 Drive motor
140 Drive shaft
141 Worm screw
15 Gear element (worm wheel)
150 Shaft
151 Detection device
152 Toothing
16 Clutch device
160, 161 Clutch element
17 Gear element
170 Shaft
18 Drive element (spindle)
180 Gear wheel
181, 182 Bearing
183 Screw thread
184 Sensor device
185 Gear wheel
186 Coupling section
19 Control device
2 Syringe
20 Cylinder tube
200 Connector
21 Piston
210 Piston head
3 Infusion line
L Longitudinal axis
P Driving direction

The invention claimed is:

1. An infusion device for administering a medical fluid to a patient, comprising:
a housing,
a receptacle arranged on the housing for receiving a syringe,
a syringe driver movable in a driving direction for acting onto a piston of the syringe received on the receptacle, and
a drive mechanism for electromotively driving the syringe driver along the driving direction, the drive mechanism comprising an electric drive motor and a rotatable drive element operatively coupled to the syringe driver for moving the syringe driver along the driving direction,
wherein the drive mechanism comprises a clutch device configured, in a coupled state, to couple the electric drive motor to the drive element such that the electric drive motor is operative to drive the drive element and, in an uncoupled state, to uncouple the electric drive motor from the drive element, and
wherein the clutch device comprises a first clutch element operatively connected to the electric drive motor and a second clutch element operatively connected to the drive element, the first clutch element and the second clutch element in the coupled state are in a rotationally fixed connection with each other by frictionally abutting each other and in the uncoupled state are disconnected from each other such that the first clutch element and the second clutch element can be moved independent of each other.

2. The infusion device according to claim 1, wherein the electric drive motor comprises a drive shaft and a worm screw arranged on the drive shaft.

3. The infusion device according to claim 2, wherein the worm screw is in engagement with a worm wheel for driving the worm wheel.

4. The infusion device according to claim 1, wherein a gearing connecting the electric drive motor to the clutch device is self-locking such that, in the coupled state of the clutch device, the drive mechanism is locked against a movement of the syringe driver in case a force is applied to the syringe driver.

5. The infusion device according to claim 1, wherein the drive element is formed by a spindle having a screw thread.

6. The infusion device according to claim 5, wherein the drive mechanism comprises a coupling element connected to the syringe driver and engaging with the screw thread of the drive element such that a rotation of the drive element is translated into a longitudinal movement of the coupling element for moving the syringe driver along the driving direction.

7. The infusion device according to claim 1, further comprising a control device for controlling the clutch device.

8. The infusion device according to claim 1, further comprising an actuation device which is actuatable by a user for transferring the clutch device from one of the coupled state and the uncoupled state to the other of the coupled state and the uncoupled state.

9. The infusion device according to claim 8, wherein the actuation device is arranged on the syringe driver.

10. The infusion device according to claim 8, wherein the actuation device is configured, in case of an actuation, to produce an actuation signal causing the clutch device to be transferred from the coupled state to the uncoupled state.

11. The infusion device according to claim 1, further comprising a sensor device arranged on the syringe driver for detecting a contact of the syringe driver with the piston of the syringe.

12. The infusion device according to claim 11, wherein the sensor device is configured, in case a contact between the syringe driver with the piston of the syringe is detected, to produce a sensor signal causing the clutch device to be transferred from the uncoupled state to the coupled state.

* * * * *